Aug. 30, 1932. W. R. PIERSON Plant Pat. 25
HYBRID TEA ROSE
Filed Nov. 30, 1931
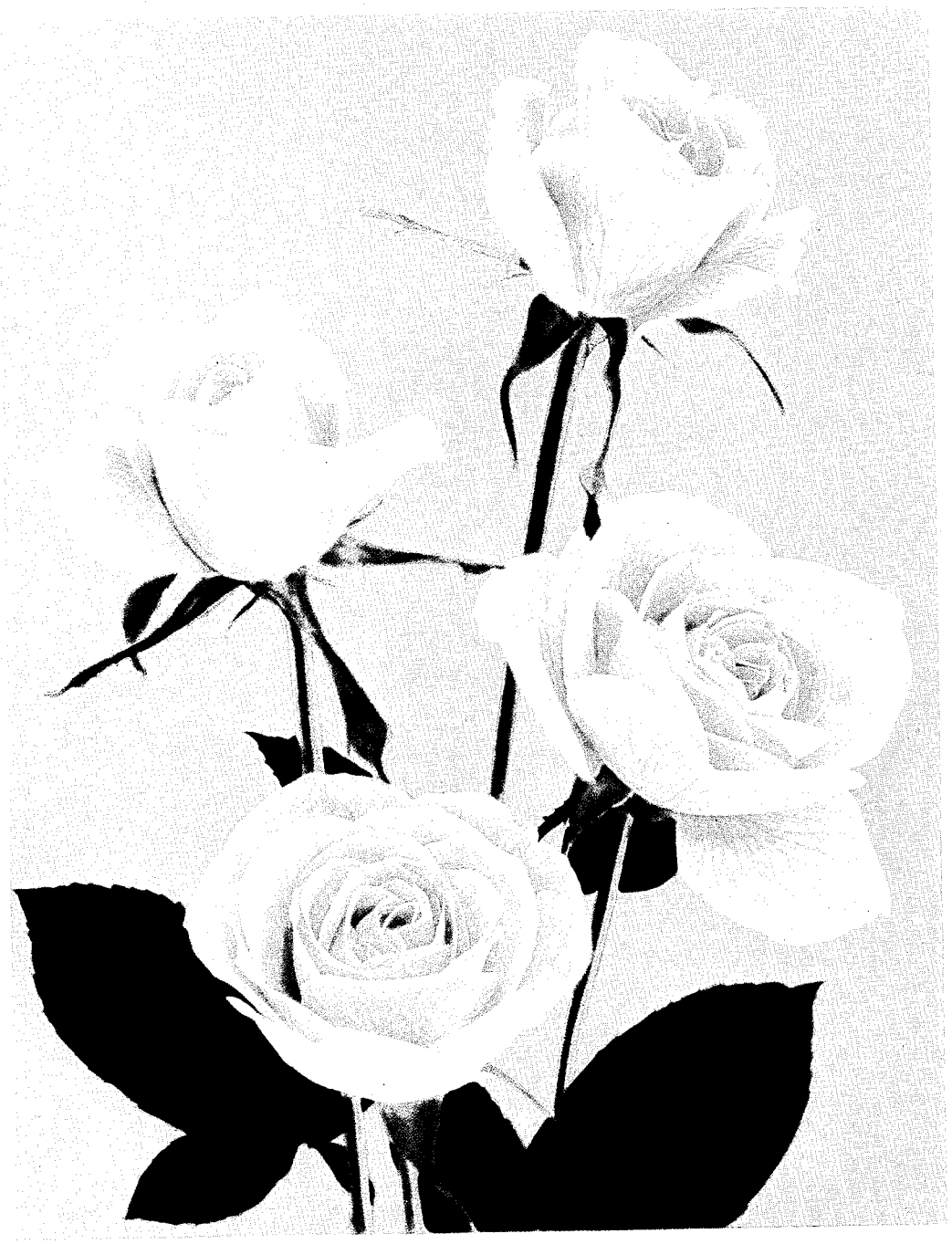
Inventor
Wallace R Pierson
By Orville M Kile
Plant Patent Agent Patented Aug. 30, 1932

Plant Pat. 25

UNITED STATES PATENT OFFICE

WALLACE R. PIERSON, OF CROMWELL, CONNECTICUT

HYBRID TEA ROSE

Application filed November 30, 1931. Serial No. 578,171.

My invention relates to improvements in fragrant, yellow, hybrid tea roses. The object of my improvements is to provide a rose of the type mentioned having a pleasing and distinctive shade of color, a high degree of fragrance, stems free of spines and thorns, pleasing foliage, vigorous growing habits, resistance to disease, and other desirable qualities.

I first discovered this new variety during or about the month of April, 1930, growing as a sport or mutation on a Talisman rose bush. I still have the parent plant growing on my grounds at Cromwell, Connecticut, producing typical Talisman roses on one-half of the plant and this new yellow variety on the other half. Following the discovery of this sport, I carefullly observed and tested it and have since reproduced from cuttings a large number of plants that show no tendency to vary from the sport parent, thus proving that this new variety is well fixed and not subject to reversions.

The accompanying illustrations show in full color two flowers approximately three-fourths opened and two flowers about one-fourth opened.

The following is a detailed description of this rose:

A bush or upright rose of medium height, vigorous of growth and resistant to disease.

Stem; slender but amply strong to support the rather heavy blossoms, forest green, free of spines or thorns for the first 8 to 10 inches below the blossom and having only a few light gray to pinkish thorns and no spines below that point. The upper stem or peduncle is straight to slightly curved but with no tendency toward the zig-zagged effect found in many varieties.

Leaves; on flower-bearing stems attaining 4 to 4½ inches in length, rather slender in form, the petioles bearing a few short hairs. The first and second leaf branches below the blossom commonly, though not always, show a tendency to develop as a single notched or cut leaf rather than two or three distinct and separated leaflets. The leaves are only moderately glossy or lustrous, medium green rather than dark green in color, flat rather than waved, and having finely serrated edges;

Stipules of medium width, sharp pointed, the points ordinarily lying close to and in same direction as the petiole of the leaf, edges beset with hairs.

Sepals; normally five and not given to extensive foliaceous development although on many specimens one or two sepals will attain a narrowly lanceolate growth.

Buds; medium length, inclined to be blunt rather than pointed, having a distinctive lemon chrome vividness which shades out to the softer strontian yellow as the bud opens.

Hips; rather large but tapering and gracefully harmonizing with the large buds and blossoms.

Flower; fragrant, large, full-petaled, double, 40 to 45 petals in October in the latitude of New York and a somewhat larger number as the weather becomes cooler, 4½ to 5 and even 5½ inches across when fully opened.

Petals vary greatly in shape from outer to inner whorls, outer petals are broadly obovate tending toward the oblanceolate in the in the center. The central petals to the number of 12 or 14 retain a closely folded or crinkled form until after the blossom is fully opened. This gives to a large percentage of the blossoms the effect of a "double center" after the blossom has opened one-fourth to two-thirds, which effect remains until the blossom is three-fourths open.

Sex organs; Stamens numerous, branched, and mounted by buff colored anthers; stigmas numerous, light yellow, touched with pink.

Color; (after flowers have been cut as buds one-fourth open and kept in water approximately 48 hours) popularly described as golden yellow. When compared with the Ridgeway color chart the color effect is approximately "lemon chrome" in the central portions of the blossom and a lighter shade or "empire yellow" on the edges of the outer petals, the bases and central portions of each petal being a more pronounced shade of yellow than the remainder and ranging from strontian yellow to lemon chrome. The intensity of color on the central and basal portion of each petal varies greatly with the angle at which it is viewed. The extreme tips of many of the outer petals bear a slight touch of pink although this is too faint to be noticeable except on close examination. The amount of pink varies somewhat with weather conditions. A few of the inner petals of some of the blossoms bear a streak of pink, but this is not visible except when the blossom is fully opened and then only on close examination. The veining of the petals though distinct is not obtrusive and there is a noticeable concentration of yellow coloring matter along the principal veins.

The chief characters which, I believe, plainly distinguish my new variety of rose from all other known varieties of yellow color and particularly from Souvenir de Claudius Pernet, are:

1. Stems free of spines and thorns for a distance of 8 to 10 inches below the blossom.
2. Leaves semi-glossy rather than highly glossy as in Souvenir de Claudius Pernet, and having finely serrated edges rather than being coarsely toothed.
3. Sepals only slightly foliaceous.
4. Color at usual cutting stage somewhat deeper yellow or more golden than in Souvenir de Claudius Pernet, also touched with slight pink only visible on careful examination.
5. Greater number of petals than in Souvenir de Claudius Pernet and having double center effect.
6. Hips less bulky and more graceful in appearance than in Souvenir de Claudius Pernet.
7. More fragrant than Souvenir de Claudius Pernet.
8. Exceptionally fine shipping and keeping qualities.

I claim:

A variety of rose as herein shown and described, characterized chiefly by its golden yellow color, full petalage, stems free of spines and thorns, and semi-glossy leaves.

WALLACE R. PIERSON.